United States Patent
Kaplan (10) Patent No.: US 10,369,220 B2
(45) Date of Patent: Aug. 6, 2019

(54) METHODS AND COMPOSITIONS FOR AFFECTING IMMUNOLOGICAL RESPONSIVENESS

(71) Applicant: CellPrint IP Holding, LLC, Cleveland, OH (US)

(72) Inventor: David R. Kaplan, Shaker Heights, OH (US)

(73) Assignee: CELLPRINT IP HOLDING, LLC, Cleveland, OH (US)

( * ) Notice: Subject to any disclaimer, the term of this patent is extended or adjusted under 35 U.S.C. 154(b) by 0 days.

(21) Appl. No.: 15/724,586

(22) Filed: Oct. 4, 2017

(65) Prior Publication Data

US 2018/0092973 A1    Apr. 5, 2018

Related U.S. Application Data

(60) Provisional application No. 62/403,862, filed on Oct. 4, 2016, provisional application No. 62/427,331, filed on Nov. 29, 2016.

(51) Int. Cl.
| | | |
|---|---|---|
| *A61K 39/39* | (2006.01) | |
| *A61K 45/00* | (2006.01) | |
| *A61K 49/00* | (2006.01) | |
| *G01N 33/50* | (2006.01) | |
| *A61K 45/06* | (2006.01) | |
| *A61K 39/00* | (2006.01) | |

(52) U.S. Cl.
CPC .............. *A61K 39/39* (2013.01); *A61K 45/06* (2013.01); *G01N 33/505* (2013.01); *G01N 33/5023* (2013.01); *G01N 33/5047* (2013.01); *A61K 39/00* (2013.01)

(58) Field of Classification Search
CPC ........ A61K 31/00; A61K 38/00; A61K 39/00; A61K 45/00
USPC .................................................. 424/9.1, 9.2
See application file for complete search history.

(56) References Cited

U.S. PATENT DOCUMENTS 6,083,985 A * 7/2000 Yonemoto ............... A61K 45/06
                                                      514/379
2013/0336928 A1* 12/2013 Kobylecky .......... A61K 9/0043
                                                      424/85.4

OTHER PUBLICATIONS

Pardoll D., The Blockade of Immune Checkpoints in Cancer Immunotherapy, Nat Rev Cancer, 2012, pp. 252-264, vol. 12(4).
Sharma, et al., The Future of Immune Checkpoint Therapy, Science, Apr. 3, 2015, pp. 56-61, vol. 348, Iss. 6230.
Michot, et al., Immune-Related Adverse Events With Immune Checkpoint Blockade: A Comprehensive Review, European J. Cancer, Feb. 2016, pp. 139-148, vol. 54.
Xiao, et al., Diagnosis and Classification of Drug-Induced Autoimmunity (DIA), J. Autoimmunity, Feb. 1, 2014, pp. 66-72, vol. 48.
Berglund, et al., Chlorpromazine-Induced Antinuclear Factors, Acta Med Scand, Jan.-Feb. 1970, pp. 67-74, vol. 187(1-2).
Mysler, et al., Ciprofloxacin Reactions Mimicking Lupus Flares, Arthritis & Rheumatism, Jul. 1994, pp. 1112-1113, vol. 37(7).
Crowson, et al., Diltiazem and Subacute Cutaneous Lupus Erythematosus-Like Lesions, New England J. Med., Nov. 23, 1995, p. 1429, vol. 333, No. 21.
Cameron, et al., The Lupus Syndrome Induced by Hydralazine: A Common Complication With Low Dose Treatment, Brit. Med. J., Aug. 18, 1984, pp. 410-412, vol. 289.
Rothfield, et al., Isoniazid Induction of Antinuclear Antibodies: A Prospective Study, Annals of Internal Med., May 1, 1978, pp. 650-652, vol. 88 (5).
Nordstrom, et al., Methyldopa-Induced Systemic Lupus Erythematosus, Arthritis & Rheumatism, Feb. 1989, pp. 205-208, vol. 32(2).
Elkayam, et al., Minocycline-Induced Autoimmune Syndromes: An Overview, Semin Arthritis Rheum, Jun. 1999, pp. 392-397, vol. 28(6).
Woosley, et al., Effect of Acetylator Phenotype on the Rate at Which Procainamide Induces Antinuclear Antibodies and the Lupus Syndrome, New England J. Med., May 25, 1978, pp. 1157-1159, vol. 298(21).
Ruger, et al., Subacute-Cutaneous Lupus Erythematosus Induced by Simvastatin, J. Dtsch Soc. Dermatol Ges., Jan. 2011, pp. 54-55, vol. 9(1).
Mbongue, et al., The Role of Indoleamine 2, 3-Dioxygenase in Immune Suppression and Autoimmunity, Vaccines (Basel), Sep. 2015, pp. 703-729, vol. 3(3).
Yoshimura, et al., SOCS Proteins, Cytokine Signalling and Immune Regulation, Nature Rev. Immunol., Jun. 2007, pp. 454-465, vol. 7(6).
Couper, et al., IL-10: The Master Regulator of Immunity to Infection, J. Immunol, May 1, 2008, pp. 5771-5777, vol. 180(9).
Kyurkchiev, et al., Secretion of Immunoregulatory Cytokines by Mesenchymal Stem Cells, World J. Stem Cells, Nov. 26, 2014, pp. 552-570, vol. 6(5).
Bachmann, et al., Interleukin 2: From Immunostimulation to Immunoregulation and Back Again, EMBO Reports, Dec. 2008, pp. 1142-1148, vol. 8(12).
Cornish, et al., Suppressor of Cytokine Signaling-1 Regulates Signaling in Response to Interleukin-2 and Other Gamma C-Dependent Cytokines in Peripheral T Cells, J. Biological Chem., Jun. 2003, pp. 22755-22761, vol. 278(25).

(Continued)

*Primary Examiner* — Rodney P Swartz
(74) *Attorney, Agent, or Firm* — Benesch, Friedlander, Coplan & Aronoff LLP (57) ABSTRACT

A method of treating a subject having a deficient immune response is described. The method includes administering a therapeutically effective amount of non-immune drug, or an analog or metabolite thereof, known to induce one or more autoimmune syndromes to the subject. Drugs known to induce one or more autoimmune syndromes, such as lupus-like syndromes, include immune checkpoint inhibitor blockers. Methods of identifying drugs capable of enhancing immunity are also described.

14 Claims, 1 Drawing Sheet

(56) References Cited

OTHER PUBLICATIONS

Li, et al. FOXP3+ Regulatory T Cells and Their Functional Regulation, Cellular Molecular Immunol., Sep. 2015, pp. 558-565, vol. 12(5).

Shang, et al., Prognostic Value of Tumor-Infiltrating FoxP3+ Regulatory T Cells in Cancers: A Systematic Review and Meta-Analysis, Sci. Rep., Oct. 2015, pp. 1-9, vol. 5, 15179.

Velazquez-Cruz, et al., Association of PDCD1 Polymorphisms With Childhood-Onset Systemic Lupus Erythematosus, Euro. J. Human Gen., Jan. 17, 2007, pp. 336-341, vol. 15.

\* cited by examiner

METHODS AND COMPOSITIONS FOR AFFECTING IMMUNOLOGICAL RESPONSIVENESS

CONTINUING APPLICATION DATA

This application claims the benefit of U.S. Provisional Application Ser. No. 62/403,862, filed Oct. 4, 2016, and U.S. Provisional Application Ser. No. 62/427,331, filed Nov. 29, 2016, the disclosures of which are incorporated by reference herein.

BACKGROUND

Immune mechanisms are responsible for a variety of maladies associated with a failure to mediate an effective immune response. Clinical circumstances that involve ineffective immune responsiveness include vaccination, vaccine failure, immunosuppression, immunodeficiency syndromes, viral infection, bacterial infection, fungal infection, parasitic infection, cancer initiation and progression, and Alzheimer's disease.

Immune checkpoint inhibition (ICI) is a mechanism involved in regulating immune responsiveness. Pardoll D., Nat Rev Cancer, 12, 252-264 (2012); Sharma P, Allison J P, Science 348, 56-61 (2015). This mechanism involves the surface membrane expression of molecules on immune cells, especially T lymphocytes, and their ligands on the surface membrane of other cells. The binding of ICI molecules transmits a negative immunoregulatory signal to T cells. In that way, immunity is down-regulated. ICI suppresses pathologic and physiological immune responses, contributing to the maintenance of immunological self-tolerance and immune homeostasis.

It is well known that some compounds enhance autoimmune phenomena as an unwanted side effect of treatments for conditions not related to immunity. However, no one has proposed the possibility of using compounds that induce autoimmune phenomenon as a side effect for treatment of conditions that would benefit from enhanced immunity, even though many of the compounds have been known to induce autoimmune phenomena for more than 40 years.

Autoimmune phenomena as a side effect of therapy have never before been associated with immune potentiation. Autoimmunity has been considered an undesirable and pathological consequence of some therapies, and adverse events such as the induction of autoimmune phenomena have been shunned, not embraced. The possibility of developing a new therapy with a drug for another indication that causes an undesirable side effect has never before been achieved.

The autoimmune phenomena associated with immune checkpoint blockade have been characterized as "immune-related adverse events" and not seen as integral to treatment, even in the case of anticancer drugs. Autoimmune responses and physiological immune responses to infection and cancer and foreign substance have been taught as distinct which explains in part the novelty in proposing using compounds that induce autoimmune phenomena to enhance physiological immune responses.

In conditions such as chronic infection and neoplasia, ICI undesirably reduces the efficacy of an immune response capable of fighting the infection or eliminating the neoplasia. Immunotherapy for malignancies has involved the interruption of ICI. Thus, blocking antibodies that bind to cell surface components of ICI effectively turn off the inhibition of the immune response. Consequently, immunity is enhanced. Both the T cell surface receptors of ICI and their ligands have been successfully targeted with this approach. Autoimmune phenomena are a consequence of PD-1 blockade for patients with cancer. Michot et al., European J Cancer, 54:139-148 (2016). Most saliently, blocking antibodies to PD-1 or its ligand PD-L1 have enhanced anti-cancer immune responses in patients and resulted in significant remissions in the cancer. At present, the tumors that have shown responses to this therapy include melanoma, renal cell carcinoma, non-small cell lung cancer, small cell lung cancer, urothelial cancer, head and neck squamous cell carcinoma, gastric cancer, hepatocellular carcinoma, esophageal cancer, colon cancer with high levels of microsatellite instability, all other tumors with high levels of microsatellite instability, Hodgkin lymphoma, non-Hodgkin lymphoma, ovarian cancer, mesothelioma, and triple negative breast cancer. Methods for modulating ICI suppressive activity are urgently required.

SUMMARY

This invention relates to compositions comprising a compound or a mixture of compounds known to induce autoimmune phenomena, such as a lupus-like syndrome, in subjects identified as or being suspected of having a deficient immune response. These compounds work by enhancing an effective immune response. The invention includes analogs, isomers, or metabolites of the compounds know to induce autoimmune phenomena in people or a mixture of analogs, isomers, or metabolites. The invention also relates to methods of treating or preventing conditions in a subject characterized by a deficient immune response such as cancer; viral infections and other microbial infections; immunodeficiency associated with aging, surgery, trauma, genetic changes, or alcoholism; Alzheimer's disease by administering a therapeutically effective amount of a non-immune compound or compounds, analogs, isomers, or metabolites to the subject. The invention further relates to methods of assessing the effectiveness of individual compounds or a mixture of compounds to enhance immune responsiveness, and methods of identifying effective compounds.

DETAILED DESCRIPTION

The invention involves a method of enhancing immune responsiveness in a subject suspected of having a deficiency of immune responsiveness. The method includes administering an effective amount of a compound or a mixture of compounds that are known to induce autoimmune phenomenon including a lupus-like syndrome, hepatitis, nephritis, pemphigus, hemolytic anemia, thrombocytopenia, vasculitis, thyroiditis, myocarditis, pneumonitis, dermatomyositis, polymyositis, lichen planus, pemphigoid, Sjogren's syndrome, glomerulonephritis, myopathy, granulomatous lung disease, anti-phospholipid syndrome, sarcoidosis, and/or Henoch-Schonlein purpura as a side effect.

Definitions

Unless otherwise defined, all technical and scientific terms used herein have the same meaning as commonly understood by one of ordinary skill in the art to which this invention pertains. In case of conflict, the present specification, including definitions, will control.

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such. Furthermore, the recitation of numerical ranges by endpoints includes all of the numbers subsumed within that range (e.g., 1 to 5 includes 1, 1.5, 2, 2.75, 3, 3.80, 4, 5, etc.).

The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "therapeutically effective" is intended to qualify the number or amount of an agent which will achieve the goal of decreasing disease severity while avoiding adverse side effects such as those typically associated with alternative therapies. A therapeutically effective amount may be administered in one or more doses. Treatments that are therapeutically effective within the meaning of the term as used herein include treatments that improve a subject's quality of life even if they do not improve the disease outcome per se.

An "effective amount" generally means an amount which provides the desired local or systemic effect, e.g., effective to stimulate immunity, including achieving the specific desired effects described in this application. For example, an effective amount is an amount sufficient to effectuate activation of an immune cell.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy. In various embodiments, the symptoms of a disease or disorder are alleviated by at least 5%, at least 10%, at least 20%, at least 30%, at least 40%, or at least 50%.

Prevention or prophylaxis, as used herein, refers to preventing the disease or a symptom of a disease from occurring in a subject who may be predisposed to the disease but has not yet been diagnosed as having it (e.g., including diseases that may be associated with or caused by a primary disease). Prevention may include completely or partially preventing the occurrence of a disease or its symptoms.

The terms "individual," "subject," and "patient" can be used interchangeably herein irrespective of whether the subject has or is currently undergoing any form of treatment. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Treatment of humans is of particular interest.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogs of natural nucleotides, as well as nucleic acid-like structures with synthetic backbones.

"Peptide" and "polypeptide" are used interchangeably herein and refer to a compound made up of a chain of amino acid residues linked by peptide bonds. An "active portion" of a polypeptide means a peptide that is less than the full length polypeptide, but which retains measurable biological activity and retains biological detection.

All scientific and technical terms used in the present application have meanings commonly used in the art unless otherwise specified. The definitions provided herein are to facilitate understanding of certain terms used frequently herein and are not meant to limit the scope of the present application.

Methods of Treating a Subject Having a Deficient Immune Response

The inventors have determined that autoimmune phenomena such as a lupus-like syndrome in patients treated with various drugs may be caused by effects on some or all molecules that mediate immunoregulation. The pharmacological effect on an immunoregulatory pathway or pathways results in enhanced immune responsiveness which is observed clinically as a lupus-like syndrome or other autoimmune phenomena. This enhanced immune responsiveness may be used in clinical situations that would benefit from increased immunity.

In one aspect, the present invention provides a method of treating a subject having a deficient immune response. A deficient immune response, as defined herein, refers to an immune response that causes the subject to have an increased risk of developing a disease or disorder that the immune system is intended to prevent. In some embodiments, the deficient immune response is associated with the development of disease in the subject. The method includes administering a therapeutically effective amount of non-immune drug, or an analog or metabolite thereof, known to induce one or more autoimmune syndromes, referred to herein as autoimmune-affecting drugs. A non-immune drug, as used herein, refers to a drug which is not indicated or characterized as a drug useful for the treatment of immune disorders, even though it may be known to have an effect on immunity, for example, a cardiovascular agent known to have the potential to cause Lupus as an undesirable side-effect is an example of a non-immune drug.

The autoimmune-affecting drugs can be used for both prophylactic and therapeutic treatment. The autoimmune-affecting drugs can, for example, be administered prophylactically to a subject prior to the development of a disease associated with a deficient immune response. Prophylactic administration, also referred to as prevention, is effective to decrease the likelihood that a deficient immune response will develop in the subject. Determination of those subjects "at risk" can be made by any objective or subjective determination by a diagnostic test or opinion of a subject or health care provider (e.g., genetic test, enzyme or protein marker, family history, and the like).

The autoimmune-affecting drugs of the invention can also be administered therapeutically to a subject that has been identified as being in need of treatment. For purposes of treatment, a subject in need of treatment includes any human or animal subject who has a disorder characterized by a deficient immune response. Such disorders include, but are not limited to cancers and pre-cancers. Identifying a subject in need of such treatment can be in the judgment of a subject or a health care professional and can be subjective (e.g. opinion) or objective (e.g. measurable by a test or diagnostic method). In one embodiment of therapeutic administration, administration of the autoimmune-affecting drugs is effective to eliminate the disease; in another embodiment, administration of the autoimmune-affecting drugs is effective to decrease the symptoms related to the disease. The autoimmune-affecting drugs may be also used in the treatment of any other disorders in which dysregulation of an immune response may be implicated.

Autoimmune-affecting drugs can be polypeptides, polynucleotides, or small organic compounds. Small organic compounds of the invention preferably have a molecular weight below 2,000 daltons, more preferably between 300 and 1,000 daltons, and most preferably between 400 and 700 daltons. It is preferred that these small molecules are organic, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The chemical candidates often comprise cyclical carbon or heterocyclic structures and/or aromatic or polyaromatic structures substituted with one or more chemical functional groups.

In some embodiments, the autoimmune-affecting drug is a drug selected from the group consisting of anti-arrhythmic drugs, anticoagulants, antihistamines, anti-seizure drugs, antihypertensive drugs, anti-inflammatory drugs, antibiotics, cholesterol-lowering drugs, hormonal drugs, laxatives, proton-pump inhibitors, psychiatric drugs, calcium channel blockers, vasodilators, anti-platelet drugs, and chelating agents. An advantage of these compounds involves their prior indication that they can be given safely to people for therapy.

Specific examples of autoimmune-affecting drugs include hydralazine, minocycline, simvastatin, sulfasalazine, minoxidil, terbinafine, diltiazem, chlorpromazine, quinidine, isoniazid, procainamide, penicillamine, fosinopril, methyldopa, cimetidine, cinnarizine, benoxaprofen, ibuprofen, mesalazine, para-amino salicylic acid, sulindac, tolmetin, golimumab, infliximab, interferon beta, interleukin 2, gold salts, cefuroxime, chlorprothixene, levomeprazine, perazine, perphanazine, reserpine, thioridazine, nalidixic acid, penicillin, streptomysin, sulfadimethoxine, sulfamethoxypyridazine, quinine, acecainide, propafenone, acebutolol, atenolol, enalapril, labetalol, metaprolol, oxprenolol, practolol, prindolol, propranolol, timolol, phenylbutazone, allopurinol, danazol, leuprolide acetate, clonidine, guanoxan, prazosin, chlorthalidone, spironolactone, aminoglutethimide, 1,2-dimethyl-3-hydroxypryridine-4-1, atorvastatin, fluvastatin, lovastatin, pravastatin, danazol, methimazole, methylthiouracil, propylthiouracil, thionamide drugs, carbamazepine, diphenylhydantoin, ethosuximide, primidone, trimethadione, normifensine, phenelzine, pheneturide, mephenytoin, phenylethylacetylurea, promethazine, pyrathiazine, anthiomaline, levodopa, metrizamide, oxyphenisatin, psoralen, tolazamide, adulimumab, certolizumab pegol, lithium carbonate, methylsergide, nitrofurantoin, clometacine, atomexitine, diclofenac, doxycycline, fenofibrate, papverine, pemoline, phenprocoumon, twinrix, verapamil, nifedipine, ticlopidine, piroxicam, naproxen, bupropion, lansoprazole, tamoxifen, feflunomide, docetaxel, efalizumab, cilazapril, fluorouracil, cyclosporine, and the combination of rifampin+pyrazinamide.

In one aspect, the present invention is directed to the use of drug, or an analog or metabolite thereof, known to induce one or more autoimmune syndromes (i.e., autoimmune affecting drugs). A number of drugs are known to induce autoimmune phenomena after short or long term therapy. These phenomena include a lupus-like syndrome that is characterized by arthralgia, myalgia, vasculitis, fatigue, and the production of auto-antibodies. Other pertinent autoimmune phenomena include autoimmune hemolytic anemia, autoimmune thrombocytopenia, autoimmune vasculitis, autoimmune hepatitis, autoimmune nephritis, autoimmune pemphigus, autoimmune thyroiditis, autoimmune pneumonitis, dermatomyositis, autoimmune polymyositis, autoimmune lichen planus, pemphigoid, autoimmune Sjogren's syndrome, autoimmune glomerulonephritis, autoimmune myopathy, autoimmune granulomatous lung disease, autoimmune anti-phospholipid syndrome, autoimmune sarcoidosis, and autoimmune Henoch-Schonlein purupura.

In some embodiments, the autoimmune syndrome is a lupus-like syndrome. Systemic lupus erythematosus (SLE), also known simply as lupus, is an autoimmune disease in which the body's immune system mistakenly attacks healthy tissue in many parts of the body. Drug-induced lupus has been observed in patients chronically treated with various drugs. A list of drugs that induced lupus in patients undergoing treatment include the following classified by their current clinical indication (see Xiao X, Chang C., J Autoimmunity, 48-49, 66-72 (2014)):

Anti-arrhythmic: procainamide, quinidine, propafenone, acecainide
Anti-seizure: phenytoin, ethotoin, carbamazepine, oxcarbazebine, diphenylhydantoin, primidone, mephenytoin, pheneturide, phenylethylacetylurea, valproate, ethosuximide, trimethadione
Antihypertensive: hydralazine, methyldopa, captopril, fosinopril, hydrochlorothiazide
Anti-inflammatory: sulfasalazine
Antibiotic: isoniazid, ciprofloxacin, minocycline, terbinafine, griseofulvin, tetracycline, levofloxacin, pyrazinamide
Cholesterol lowering: simvastatin, atorvastatin, fluvastatin, lovastatin, pravastatin, fenofibrate
Psychiatric/Neuro: chlorpromazine, perphanazine, chlorprothixene, levomeprazine, perazine, reserpine, thioridazine, lithium carbonate, normifensine, phenelzine, bupropion, atomexitine, levodopa, methylsergide
Calcium channel block: diltiazem, verapamil, nifedipine
Vasodilatory: minoxidil, papverine
Anti-Platelet: ticlopidine
Chelating: D-penicillamine There are additional drugs that are known to induce more diverse autoimmune phenomenon such as autoimmune hemolytic anemia, autoimmune thrombocytopenia, autoimmune vasculitis, autoimmune hepatitis, autoimmune nephritis, autoimmune pemphigus, autoimmune thyroiditis, autoimmune pneumonitis, dermatomyositis, autoimmune polymyositis, autoimmune lichen planus, pemphigoid, autoimmune Sjogren's syndrome, autoimmune glomerulonephritis, autoimmune myopathy, autoimmune granulomatous lung disease, autoimmune anti-phospholipid syndrome, autoimmune sarcoidosis, and autoimmune Henoch-Schonlein purpura. The drugs or a subset of the drugs that induce these autoimmune syndromes can also be used to enhance immune responsiveness.

In some embodiments, the autoimmune-affecting drug is a drug known to induce one or more autoimmune syndromes other than lupus or a lupus-like syndrome. A listing of drugs that have been shown to induce one or more autoimmune syndromes other than lupus follows, wherein the drugs are classified by their current clinical indication:

Antihistamine: cimetidine, cinnarizine, promethazine, pyrathiazine

Anti-inflammatory: benoxaprofen, ibuprofen, mesalazine, para-amino salicylic acid, sulindac, tolmetin, gold salts, piroxicam, naproxen, diclofenac, cyclosporine, phenylbutazone, leflunomide, clometacine Antibiotic: cefuroxime, nitrofurantoin, penicillin, doxycycline, streptomysin, sulfadimethoxine, sulfamethoxypyridazine, quinine, nalidixic acid, twinrix, rifampin+pyrazinamide, anthiomaline Antihypertensive: labetalol, metaprolol, oxprenolol, practolol, prindolol, propranolol, timolol, clonidine, atenolol, enalapril, cilazapril, acebutolol, guanoxan, prazosin, chlorthalidone, spironolactone Hormonal: methimazole, methylthiouracil, propylthiouracil, thionamide drugs, danazol, leuprolide acetate 1,2-dimethyl-3-hydroxypryridine-4-1, tolazamide, aminoglutethimide, tamoxifen, glyburide Anti-Acid: lansoprazole Laxative: oxyphenisatin Anticoagulant: phenprocoumon Gout/kidney stones: allopurinol It is important to note that many autoimmune-affecting drugs can be categorized under more than one clinical indication. Also, many of the drugs induce a lupus-like syndrome and other autoimmune phenomena. Chang C, Gershwin M E, Drug Safety, 34, 357-374 (2011). Since immune potentiation is most closely related to the induction of a lupus-like syndrome, the compounds that are most closely associated with the induction of a lupus-like syndrome are favored for the development of immune potentiating capability. Compounds most associated with the induction of a lupus-like syndrome, which are preferred autoimmune-affecting drugs, along with a reference describing this activity, are: chlorpromazine (Berglund et al., Acta Med Scand, 187:67-74 (1970)); ciprofloxacin (Mysler et al., Arthritis & Rheumatism 37:1112-1113 (1994)); diltiazem (Crowson A N, Magro C M, N. Engl J. Med 333:1429 (1995)); hydralazine (Cameron H A, Ramsay L E, Brit Med J., 289:410-412 (1984)); isoniazid (Rothfield et al., Annals Int Med, 88:650-652 (1978)); methyldopa (Nordstrom et al., Arthritis & Rheumatism 32:205-208 (1989)); minocycline (Elkayam et al., Semin Arthritis Rheum 28, 392-397 (1999)); procainamide (Woosley et al., N Engl J Med 298:1157-1159 (1978)); and simvastatin (Ruger et al., J. Dtsch Dermatol Ges. 9 (1), 54-5 (2011).

In some embodiments, a plurality of drugs known to induce one or more autoimmune syndromes are administered to the subject. For example, two different drugs known to induce one or more autoimmune syndromes can be administered to the subject. In some embodiments, the plurality of autoimmune-affecting drugs exhibit additive or synergistic effects. For example, the combination of drugs can exhibit activity 5%, 10%, 15%, 20%, 25%, 30%, 35%, 40%, 45%, 50%, 60%, 70%, 80%, 90%, 100%, 150%, 200%, or greater than 200% compared to the activity of the drugs when administered separately.

The term "drug" is used herein to describe any specific drug disclosed herein, including any and all active stereoisomers (including diasteromers), individual optical isomers (enantiomers) or racemic mixtures, pharmaceutically acceptable salts and prodrug forms. Within its use in context, the term compound may refer to a single compound or a mixture of compounds as otherwise described herein. In some embodiments, only the standard stereoisomers of the drug are used.

Analogs, isomers, and/or metabolites of these drugs may also be used to induce activation of the immune system. An advantage of using analogs, isomers, and/or metabolites is the potential to be compounds that increase their capacity to enhance immune responsiveness in people and that decrease unwanted off-target effects. For instance, a compound that was originally developed for anti-hypertensive activity with unwanted immune potentiation as an unwanted side effect may be used to find analogs, isomers, and/or metabolites that demonstrate increased immune potentiation effects and decreased off-target anti-hypertensive activity. The drugs that have been shown to induce a lupus-like syndrome or other autoimmune phenomena as unwanted side effects have disparate original therapeutic purposes. For instance, some are antibiotics and others are indicated for treatment of hypertension or seizures. In some embodiments, it may be useful to select compounds for their activity to enhance immunity and/or for their antihypertensive, antibiotic, or anti-seizure effects.

By "analog" is meant a molecule that is not identical, but has analogous functional or structural features. For example, an analog retains the biological activity of a corresponding drug, while having certain chemical modifications that enhance the analog's function relative to the original drug. Such biochemical modifications could increase the analog's activity, or alter its pharmacokinetics or side effects. Analogs typically are based on a structurally similar backbone structure, but will differ in a particular chemical moiety. Alcohols and esters represent analogs, differing in the presence of a hydrogen atom and an alkyl group.

In some embodiments, the analogs are homologs. Homologs are compounds that form a part of a series, differing from one another by the successive addition of the same chemical moiety, e.g. a —$CH_2$— moiety. For example, ethanol ($CH_3CH_2OH$) and n-propanol ($CH_3CH_2CH_2OH$) represent homologous alcohols. The close structural similarity of these adjacent homologs gives rise to the presumption that the skilled artisan would expect these compounds to possess similar properties.

Metabolites, as used herein, refer to active drug metabolites. An active metabolite results when a drug is metabolized by the body into a modified form which continues to produce effects in the body. Usually these effects are similar to those of the parent drug but weaker, although they can still be significant, and in some cases the metabolite is more active than the administered drug. Drugs metabolites can be readily identified by those skilled in the art, using methods such as HPLC and mass spectrometry.

The list of currently available drugs that induce autoimmune phenomena in patients is not meant to be exhaustive. Drugs may be added as new agents are used and information is gathered.

Peptide Drugs

In some embodiments, the autoimmune-affecting drug is a peptide or a peptide derivative. In further embodiments, the peptide is capable of interfering with a molecule involved in ICI. In some embodiments, the peptides can include a protein transduction domain (e.g., a TAT domain) that facilitates passage across the cell membrane. The invention further provides peptide derivatives (e.g., peptidomimetics), which include cyclic peptides, peptides obtained by substitution of a natural amino acid residue by the corresponding D-stereoisomer, or by a unnatural amino acid residue, chemical derivatives of the peptides, dual peptides, multimers of the peptides, and peptides fused to other proteins or carriers. In one example, a peptide derivative is more resistant to proteolytic degradation than the corresponding non-derivatized peptide. For example, a peptide derivative having D-amino acid substitution(s) in place of one or more L-amino acid residue(s) resists proteolytic cleavage. In another example, the peptide derivative has increased permeability across a cell membrane as compared to the corresponding non-derivatized peptide. For example, a peptide derivative may have a lipophilic moiety coupled at the amino terminus and/or carboxyl terminus and/or an internal site. Such derivatives are highly preferred when targeting intracellular protein-protein interactions, provided they retain the desired functional activity. In another example, a peptide derivative binds with increased affinity to a ligand (e.g., an ICI receptor or ligand).

The peptides or peptide derivatives of the invention are obtained by any method of peptide synthesis known to those skilled in the art, including synthetic and recombinant techniques. For example, the peptides or peptide derivatives can be obtained by solid phase peptide synthesis. Such solid phase syntheses have been described, for example, by Merrifield, J. Am. Chem. Soc. 85:2149, 1964; Vale et al., Science 213:1394-1397, 1984; Marki et al., J. Am. Chem. Soc. 10:3178, 1981, and in U.S. Pat. Nos. 4,305,872 and 4,316,891. In some embodiments, an automated peptide synthesizer can be employed.

Immune Checkpoint Inhibition

The various drugs that induce autoimmune phenomena can mediate this effect through a variety of distinct mechanisms. Some drugs that cause a lupus-like syndrome or autoimmune phenomena affect a specific immunoregulatory pathway or more than one immunoregulatory pathway. For instance, a drug that induces autoimmune phenomena may inhibit expression of an ICI molecule on the cell surface or it may block the downstream signal transduction pathway associated with ICI ligation events. The disruption of an immunoregulatory pathway by a drug that induces autoimmune phenomena represents a drug candidate that can be developed to enhance immune responsiveness in patients with inadequate immunity. The enhanced immune responsiveness can be, for example, a 5%, 10%, 15%, 20%, 25%, 30%, 35%, 40%, 45%, 50%, 60%, 70%, 80%, 90%, 100%, 150%, 200%, or a more than 200% increase in immune responsiveness.

In some embodiments, the drug is an immune checkpoint inhibitor blocker (i.e., a drug that interferes with ICI). There are several ICI receptors and ligands. Nirschl C J, Drake C G., Clin Cancer Res 19:4917-4924, 2013; Tsai H-F, Hsu P-N., J Biomed Sci. 24 (1):35 (2017). Table 1 includes some ICI molecular pairs but it is not meant to be a complete compilation. Additionally, new ICI receptors and ligands are expected to be discovered.

TABLE 1

| ICI molecular pairs | |
|---|---|
| Inhibitory receptors on T cells | Ligands on other cells |
| CTLA-4 (CD152) | CD80; CD86 (B7-1; B7-2) |
| PD-1 (CD279) | PD-L1 (CD274); PD-L2 (CD273) |
| VEGFR | VEGF-A |
| Lag3 | MHC class II |
| TIM-3 | galectin-9; phosphatidylserine |
| CD160 | MHC class I; herpes virus entry mediator |
| TNFRSF25 | TRAIL |
| CEACAM1 | carcinoembryonic antigen subgroup members |
| TIGIT | CD155; CD112 |
| CD48 | CD244 |
| CD47 | SIRPα |
| CD40L (CD154) | CD40 |
| 4-1BB (CD137) | 4-1BB Ligand (CD137L) |
| GITR | GITR ligand |
| CD226 | — |
| CD270 (HVEM) | — |
| CD134 | CD134 ligand |
| CD278 (ICOS) | — |
| CD155 (poliovirus receptor) | — |
| Adenosine A2A receptor | — |
| Fas (CD) | Fas Ligand (CD |

CTLA4 = cytotoxic T lymphocyte-associated protein 4 = CD152
Lag3 = lymphocyte-activation gene 3 = CD223
Tim3 = T cell immunoglobulin and mucin-domain containing 3
CEACAM1 = carcinoembryonic antigen-related cell adhesion molecule 1 = CD66a
TIGIT = T cell immunoreceptor with Ig and ITIM domains
TNFRSF25 = tumor necrosis factor receptor superfamily member 25 = death receptor 3
TRAIL = TNF-related apoptosis-inducing ligand = TNFSF10 = TNF superfamily member 10
SIRPα = signal regulatory protein α
GITR = glucocorticoid induced TNFR-related protein
HVEM = herpesvirus entry mediator
ICOS = inducible T-cell costimulator Besides ICI molecules that are expressed on the cell surface, there are immunoregulatory pathways found inside of cells. For instance, indoleamine 2,3-dioxygenase (IDO) and tryptophan 2,3-dioxygenase (TDO) are enzymes that catalyze the oxidation of L-tryptophan to N-formylkynurenine. Mbongue et al., Vaccines (Basel), 3 (3):703-29 (2015). IDO and TDO modulate the immune response by enhancing the levels of kynurenine. Inhibitors to IDO and TDO are being developed to enhance immune responsiveness. SOCS1 and SOCS3 (suppressors of cytokine signaling) are intracellular molecules that act to attenuate cytokine signaling. Yoshimura et al., Nature Rev Immunol, 7:1-12 (2007). They are known to act as important regulators of both innate and adaptive immunity.

Cytokines are a small protein (~5-20 kDa) involved in cell signaling, and in particular immunomodulation. Examples of cytokines include chemokines, interferons, interleukins, lymphokines, and tumor necrosis factors. Cytokines such as IL-10, IL-6, TGFβ, MCP-1 (CCL2), and RANTES (CCL5) are well-known to mediate immunoregulatory effects on immune cells. Couper et al., J Immunol, 180:5771-5777 (2008); Kyurkchiev et al., World J Stem Cells, 6:552-570 (2014). Cytokines are also known to exhibit a variety of activities that can include immunoregulatory effects. For instance, IL-2 is a growth factor for T lymphocytes in activation but it also acts to enhance cell death as a mechanism to downregulate immunity. Bachmann M F, Oxenius A, EMBO Reports, 8, 1142-1148 (2007). IL-2 also induces the transcription of suppressor of cytokine signaling-1 (SOCS1). Cornish et al., J Biol Chem, 278:22755-22761 (2003).

It is known that a lupus-like autoimmune disease develops in mice where the programmed cell death protein 1 (PD-1) gene has been disrupted. Hishimua et al, Immunity, 11:141-151 (1999). Additionally, in humans PDCD1 (the gene encoding PD-1) polymorphisms are associated with susceptibility to systemic lupus erythematosus. Cruz et al., Eur J Hum Genet., 15 (3), 336-41 (2007). Accordingly, PD-1 is another receptor that can play a role in autoimmune effects.

Finally, immunoregulatory effects can be mediated by specific cellular subsets such as regulatory T cells (Tregs), which are CD4+/FoxP3+ T cells. Li et al., Cellular Molecular Immunol, 12:558-565 (2015). These cells are specialized to downregulate immune responses. For instance, elevated numbers of Tregs in the tumor microenvironment is a poor prognostic factor for patients with cancer. Shang et al., Sci Rep., 5:15179 (2015).

The use of compounds to enhance immune responsiveness is not confined by the precise mechanism. The drugs may affect ICI or specific cytokines or various intercellular interactions or specific intracellular molecules that regulate immunity. The drugs may affect one or more of these mechanisms in combination or singly.

Diseases Associated with Deficient Immunity

The invention involves the identification of subjects that would benefit from an increase in immune responsiveness, such as subjects having a deficient immune response. In some embodiments, the subject has a disease associated with a deficient immune response. By "disease" is meant any condition or disorder that damages or interferes with the normal function of a cell, tissue, or organ. In some embodiments, the subject has a disease responsive to immune stimulation Clinical situations that would benefit from increased immunity include cancer; cancer prevention; infections with micro-organisms such as parasites, fungi, or bacteria; infections with viruses; immunodeficiency states such as primary immunodeficiencies; immunodeficiency acquired from infections; immunosuppression caused by aging, alcoholism, trauma, or surgery; immunosuppression caused by therapeutic measures or transplantation, splenectomy, diabetes, hepatic insufficiency, or protein-losing enteropathy; Alzheimer's disease; and vaccination. Accordingly, in some embodiments, the disease responsive to immune stimulation is selected from the group consisting of cancer, infection, immunodeficiency, immunosuppression, and Alzheimer's disease. In further embodiments, the subject does not have a disease or disorder other than the disease responsive to immune stimulation.

In some embodiments, the subject has been diagnosed with cancer. Cancer is a disease of abnormal and excessive cell proliferation, and is also associated with a deficient immune response to the cancer cells. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells.

Examples of types of cancer that can be treated using autoimmune affecting drugs include cancers, such as acoustic neuroma, acute leukemia, acute lymphocytic leukemia, acute monocytic leukemia, acute myeloblastic leukemia, acute myelocytic leukemia, acute myelomonocytic leukemia, acute promyelocytic leukemia, acute erythroleukemia, adenocarcinoma, angiosarcoma, astrocytoma, basal cell carcinoma, bile duct carcinoma, bladder carcinoma, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, colon cancer, colon carcinoma, craniopharyngioma, cystadenocarcinoma, embryonal carcinoma, endotheliosarcoma, ependymoma, epithelial carcinoma, Ewing's tumor, glioma, heavy chain disease, hemangioblastoma, hepatoma, Hodgkin's disease, large cell carcinoma, leiomyosarcoma, liposarcoma, lung cancer, lung carcinoma, lymphangioendotheliosarcoma, lymphangiosarcoma, macroglobulinemia, medullary carcinoma, medulloblastoma, melanoma, meningioma, mesothelioma, myxosarcoma, neuroblastoma, non-Hodgkin's disease, oligodendroglioma, osteogenic sarcoma, ovarian cancer, pancreatic cancer, papillary adenocarcinomas, papillary carcinoma, pinealoma, polycythemia vera, prostate cancer, rhabdomyosarcoma, renal cell carcinoma, retinoblastoma, schwannoma, sebaceous gland carcinoma, seminoma, small cell lung carcinoma, squamous cell carcinoma, sweat gland carcinoma, synovioma, testicular cancer, uterine cancer, Waldenstrom's fibrosarcoma, and Wilm's tumor.

In some embodiments, the subject has primary or secondary immunodeficiency or immunodeficiency acquired from infection. Most cases of immunodeficiency are secondary immunodeficiency, which are acquired due to extrinsic factors that affect the patient's immune system. Examples of these extrinsic factors include HIV infection, extremes of age (e.g., newborns and the elderly), and environmental factors, such as nutrition. In the clinical setting, the immunosuppression by some drugs, such as steroids, can be either an adverse effect or the intended purpose of the treatment. Immunosuppression can be used in organ transplant surgery as an anti-rejection measure and in patients suffering from an overactive immune system, as in autoimmune diseases.

Primary immunodeficiencies are disorders in which part of the body's immune system is missing or does not function normally. To be considered a primary immunodeficiency, the cause of the immune deficiency must not be secondary in nature (i.e., caused by other disease, drug treatment, or environmental exposure to toxins). Most primary immunodeficiencies are genetic or congenital disorders; the majority are diagnosed in children under the age of one, although milder forms may not be recognized until adulthood. Examples of primary immunodeficiencies include combined T and B-cell immunodeficiencies, antibody deficiencies, diseases of immune dysregulation, congenital defects of phagocyte number, and/or function, defects in innate immunity, autoinflammatory disorders, and various other well-defined immunodeficiency syndromes such as Wiskott-Aldrich syndrome, DiGeorge syndrome, Hermansky-Pudlak syndrome, and hyper-IgE syndrome.

In some embodiments, the subject has secondary immunodeficiency. For example, the subject may have immunosuppression caused by aging, alcoholism, trauma, surgery, transplantation, splenectomy, diabetes, infection, hepatic insufficiency, or protein-losing enteropathy.

In some embodiments, the subject has been diagnosed with a viral infection. An effective immune response is one of the only real ways to eliminate a viral infection. Examples of human viruses include but are not limited to: Retroviridae (e.g. human immunodeficiency viruses, such as HIV-1 (also referred to as HDTV-III, LAVE or HTLVIII/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus).

In some embodiments, the subject has been diagnosed with a bacterial infection. An effective immune response is critical for responding to a bacterial infection. Exemplary bacterial pathogens include *Aerobacter, Aeromonas, Acinetobacter, Actinomyces israelii, Agrobacterium, Bacillus, Bacillus anthracis, Bacteroides, Bartonella, Bordetella, Bortella, Borrelia, Brucella, Burkholderia, Calymmatobacterium, Campylobacter, Citrobacter, Clostridium, Clostridium perfringens, Clostridium tetani, Corynebacterium, Corynebacterium diphtheriae, Corynebacterium sp., Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasteurella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio*, and *Yersinia*.

Vaccination

In some embodiments, the method of treating a subject having a deficient immune response includes the step of vaccinating the subject. By increasing the immune response of a subject, the autoimmune-affecting drug(s) can increase the effectiveness of vaccination. This can be particularly useful where a subject has previously suffered from vaccine failure (i.e., the failure of administration of a vaccine to increase the immunity of the subject against the particular antigen being administered, or the failure of administration of the vaccine to prevent occurrence of the disease which vaccination was intended to prevent).

Therapeutic compositions that reduce immune checkpoint inhibition (ICI) are useful alone or in combination with conventional therapies for the treatment of a deficient immune response. In some embodiments, an autoimmune-affecting drug is useful to enhance the efficacy of a vaccine, such as an antitumor vaccine or an antiviral vaccine. Vaccines comprising antigens such as tumor antigens are useful as therapeutics for the treatment of various types of diseases associate with a deficient immune response, such as cancer. In the case of cancer, these vaccines may be tailored to treat the cancers of particular individuals, by generating vaccines that target specific tumor antigens expressed on a tumor in a subject. Methods of the invention are particularly useful because they provide methods for increasing the efficacy of an immune response against a tumor antigen. Vaccines typically contain inactivated pathogenic particles or antigens that stimulate a patient's immune system. The immune system responds to this stimulation by generating immunoresponsive cells that target the antigens present in the vaccine. As described herein, ICI acts to suppress an immune response. In the case of vaccination, this suppressive activity can be undesirable. The invention provides methods for enhancing the efficacy of an immune response against a vaccine or other immunogenic composition comprising an antigen associated with disease.

Vaccines are produced using standard methods known in the art. Such vaccines contain antigens capable of stimulating the immune system. By injecting these antigens into a subject, the immune system produces antibodies or cytotoxic T lymphocytes to attack the diseased cells (e.g., cancer cells) that carry that specific antigen. Multiple antigens can be used in this type of vaccine to vary the immune system response. The invention provides therapeutic compositions and methods that may be used alone or in combination with a vaccine for the treatment of disease associated with immune deficiency in a subject.

Combination Therapies

In some embodiments, the method further comprises administered a therapeutically effect amount of a pharmaceutical agent for treatment of the disease to the subject. Autoimmune-affecting drugs can be administered alone or in combination with any other standard therapy. In one embodiment, an agent that enhances an immune response (e.g., one that reduces Treg suppressive activity) is administered in combination with a standard therapy for the disease being treated. Such methods are known to the skilled artisan, and in the case of cancer, include, but are not limited to, chemotherapy, hormone therapy, immunotherapy, radiotherapy, and any other therapeutic method used for the treatment of cancer.

In another approach, an agent that enhances an immune response against a pathogen is administered in combination with a conventional therapy for pathogen infection. Such therapies include antibiotics or therapeutic vaccines for the treatment or prevention of a pathogen infection. In still other embodiments, compositions and methods of the invention are used in combination with standard therapies for autoimmune or inflammatory diseases and disorders. Such therapies include, but are not limited to, steroid treatment, Anti-TNF antibodies or soluble TNF agents, monoclonal antibodies against B cells, and immunosuppressive drugs like methotrexate, imuran, and others.

Monitoring Immune Responsiveness

Another aspect of the present invention involves assessing the patients or mammals for immune responsiveness after being given autoimmune-affecting drug. Methods for assessing immune responsiveness are well-known to persons skilled in the art. These measures include the assessment of antibody or cytokine levels in serum and/or flow cytometric analysis of peripheral blood immune cells. Accordingly, in some embodiments, the method further comprises taking one or more blood samples to monitor the immune responsiveness of the subject.

Immune responsiveness can be readily assessed by an evaluation of peripheral blood obtained from persons given drugs or analogs that induce autoimmune phenomena. The evaluation can be carried out in vivo, or in vitro. Immune activation can be evaluated by the levels of cytokines or chemokines present in sera or plasma. Additionally, immune responsiveness can be assessed by the expression of cytokines or chemokines or other immune effectors molecules associated with specific immune cellular subsets of cells found in the peripheral blood. Immune activation can also be ascertained by the expression of activation molecules on the surface of immune cells of specific cellular subpopulations from the peripheral blood. The absolute number of immune cells and the relative proportion of various immune cell subsets are also indicators of immune responsiveness. Evaluations with reagents that identify immune cells with certain antigenic specificities of interest that also indicators of immune response.

Immune responsiveness can be readily assessed in a culture of immune cells obtained from the peripheral blood using well-known activators of cellular immunity such as peptide antigens, bacterial superantigens, plant lectins that act as mitogens, antibodies that ligate specific cell surface molecules such as CD2, CD3, or OX4O. Indicators of immune responsiveness may include the cellular proliferation by tritiated thymidine incorporation, dye dilution, cytokine production and/or secretion, and expression levels of immune mediators such as perform or granzyme B. Enhanced immune responsiveness can be assessed by these tests.

Identification of Autoimmune-Affecting Drugs

In another aspect, the present invention is directed to methods of identifying drugs (i.e., autoimmune-affecting drugs) that enhance immunity by interrupting immune checkpoint inhibition or other mechanisms of drug-induced immunity. These methods are valuable to develop additional compounds for the treatment of patients that would be benefitted by enhanced immunity. These patients would include those having a deficient immune response, including, but not be limited to, people with cancer progression, vaccination, failed vaccination, microbial infections, immunodeficiency, or immunosuppression. The drugs or a subset of the drugs that induce these autoimmune syndromes may be assessed for their usefulness in enhancing immune responsiveness by specifically inhibiting the various immunoregulatory pathways of immune cells. Alternately, additional autoimmune-affecting drugs can be identified based on clinical observation of drugs used for other indications, where observation of immune syndrome (e.g., lupus-like) side-effects suggest that the drug may be a candidate autoimmune-affecting drug.

Figure 1:
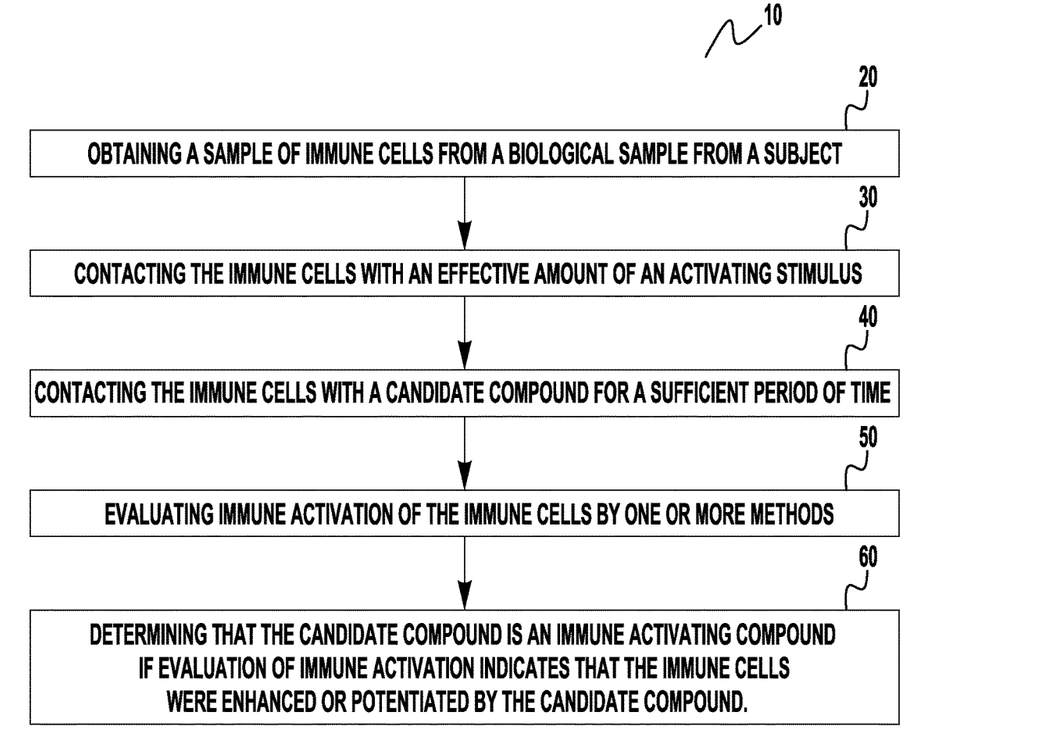
FIG. 1 provides a flowchart 10 showing the steps involved in identifying an immune activating compound. These steps include: (a) obtaining a sample of immune cells 20, (b) contacting the immune cells with an activating stimulus 30, (c) contacting the immune cells with a candidate compound 40, (d) evaluating immune activation of the immune cells 50, and (e) determining if the candidate compound is an immune activating compound 60.

A method of identifying a drug capable of enhancing immunity 10 is shown in FIG. 1. The method includes the steps of (a) obtaining a sample of immune cells from a biological sample from a subject 20; (b) contacting the immune cells with an effective amount of an activating stimulus 30; (c) contacting the immune cells with a candidate compound for a sufficient period of time 40; (d) evaluating immune activation of the immune cells 50; and (e) determining that the candidate compound is an immune activating compound if step (d) indicates that the immune cells were enhanced or potentiated by the candidate compound 60.

The method of identifying autoimmune-affecting drugs includes the step of obtaining a sample of immune cells from a biological sample from a subject Immune cells include white blood cells such as neutrophils, eosinophils, basophils, lymphocytes, and monocytes. Immune cells also include variants and differentiated forms of these cells, such as B-lymphocytes, T-lymphocytes, macrophages, and natural killer cells. Because of their importance in immune checkpoint inhibition, in some embodiments, the immune cells are T-lymphocytes (i.e., T-cells).

Biological samples that include immune cells include, but are not necessarily limited to tissue and/or fluid obtained from the spleen or thymus, and blood-related samples (e.g., whole blood, serum, plasma, and other blood-derived samples). In some embodiments, the biological sample is a biological fluid such as blood, lymphatic fluid, cerebral spinal fluid, bronchoalveolar lavage, and the like.

A biological sample may be fresh or stored (e.g. blood or blood fraction stored in a blood bank). Samples can be stored for varying amounts of time, such as being stored for an hour, a day, a week, a month, or more than a month. When samples are stored, it may be preferable to freeze the sample. The biological sample may be a bodily fluid expressly obtained for use in the invention or a bodily fluid obtained for another purpose which can be sampled for the assays of this invention. In some embodiments, it may be preferable to filter, centrifuge, or otherwise pre-treat the biological sample to remove impurities or other undesirable matter that could interfere with analysis of the biological sample.

The method of identifying autoimmune-affecting drugs also includes the step of contacting the immune cells with an effective amount of an activating stimulus. Contacting, as used herein, refers to causing two items to become physically adjacent and in contact, or placing them in an environment where such contact will occur within a reasonably short timeframe. For example, contacting an immune cell with an activating stimulus includes placing the activating stimulus in an assay system such that it will interact with immune cells and thereby activate them.

Immune activators include antigen, mitogens, and ligands of the T cell antigen receptor complex. These activators are essential for immune responsiveness but in some circumstances the activation is suboptimal. In these circumstances it is valuable to include an immune potentiator. Antibodies that block PD1 ligation are immune potentiators that have shown to be efficacious for the treatment of patients with some types of cancer. Immune potentiators enhance the immune response initiated by an activating substance (such as antigen, mitogens, or ligands of the T cell antigen receptor complex).

The method of identifying autoimmune-affecting drugs also includes the step of contacting the immune cells with a candidate compound for a sufficient period of time. A sufficient period of time, as defined herein, is an amount of time sufficient for the candidate compound to exhibit an effect on the immune cells of the biological sample. The amount of time that is sufficient can vary depending on the nature of the candidate compound and the immune cell, as well as other conditions within the biological sample, such as the concentration of immune cells and/or the candidate compound. In some embodiments, a sufficient period of time is 2 hours, 4, hours, 8 hours, 12 hours, 16 hours, 24 hours, 36 hours, 3 days, 4 days, 5 days, 6 days, or 7 days. The amount of time that is sufficient for a particular candidate compound can be readily determined by one skilled in the art.

Chemical candidates are obtained from a wide variety of sources, as will be appreciated by those in the art, including libraries of synthetic or natural compounds. As will be appreciated by those in the art, embodiments of the invention provide a method for screening any library of chemical candidates, including the wide variety of known combinatorial chemistry-type libraries. The method can be used to identify a wide variety of different types of drugs capable of enhancing immunity. For example, candidate drugs can include polypeptides, polynucleotides, or small organic compounds, as described herein. In some embodiments, the candidate compound is an analog, metabolite, or isomer of a drug known to induce one or more autoimmune syndromes. Preferably, candidate compounds are non-immune drugs which are indicated for treatment of non-immune disease.

In certain aspects, chemical candidates are synthetic compounds. A number of techniques are available for the random and directed synthesis of a wide variety of organic compounds and biomolecules, including expression of randomized oligonucleotides. Alternatively, other aspects use libraries of natural compounds in the form of bacterial, fungal, plant and animal extracts that are available or readily produced. Moreover, natural or synthetically produced libraries and compounds are readily modified through conventional chemical, physical and biochemical means. Known pharmacological agents may be subjected to directed or random chemical modifications, including enzymatic modifications, to produce structural analogs.

Where the chemical candidates are proteins, they may be naturally occurring proteins or fragments of naturally occurring proteins. Thus, for example, cellular extracts containing proteins, or random or directed digests of proteinaceous cellular extracts, may be tested. In this way libraries of prokaryotic and eukaryotic proteins may be made for screening against any number of compositions. Particularly preferred in this embodiment are libraries of bacterial, fungal, viral, and mammalian proteins, with the latter being preferred, and human proteins being especially preferred.

In other aspects, the chemical candidates are peptides ranging in size from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. The term "randomized" is intended to mean that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

Where the embodiment uses a library, the library should provide a sufficiently structurally diverse population of randomized agents to effect a probabilistically sufficient range of diversity to allow interaction with a particular immune component, such as an ICI molecule. Accordingly, an interaction library must be large enough so that at least one of its members will have a structure that interacts with an immune component. Those skilled in the art would understand how to best construct a sufficiently large and diverse library.

Further embodiments relate to a fully randomized library, with no sequence preferences or constants at any position. In other aspects, the library is biased, wherein some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In some aspects, the chemical candidates are nucleic acids. With reference to chemical candidates, "nucleic acid" or "oligonucleotide" used herein means at least two nucleotides covalently linked together. Embodiments composed of nucleic acids will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite linkages, and peptide nucleic acid backbones and linkages. Other analog nucleic acids include those with positive backbones; non-ionic backbones, and non-ribose backbones. Nucleic acids containing one or more carbocyclic sugars are also included within the definition of nucleic acids. These modifications of the ribose-phosphate backbone may be done to facilitate the addition of additional moieties such as labels, or to increase the stability and half-life of such molecules in physiological environments. As will be appreciated by those in the art, all of these nucleic acid analogs may find use in various inventive embodiments. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

Further embodiments include chemical candidates that are organic molecules or chemicals with organic moieties, wherein the molecule or moiety can be synthesized from a series of substrates that can be chemically modified. "Chemically modified" includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, heteroatom bearing compounds, amino acids, and nucleosides. Chemical (including enzymatic) reactions may be carried out on the candidate compounds to form new substrates or agents that can then be tested in various embodiments. In some embodiments, the candidate compounds are drugs, or the analogs or metabolites of drugs, that have already been identified for treatment of non-immune diseases.

As will be appreciated by those in the art, it is possible to screen more than one type of chemical candidates at a time. Thus, the library of chemical candidates used may include only one type of agent (i.e. peptides), or multiple types (peptides and organic agents).

The method of identifying autoimmune-affecting drugs also includes the step of evaluating immune activation of the immune cells. A variety of methods are known to those skilled in the art for evaluating the activation of immune cells. For example, the method of activating immune cells can be selected from methods including: (i) evaluating the degree of proliferation by the immune cells by assessing dye dilution; (ii) evaluating the level of cytokine or chemokine release by the immune cells; (iii) evaluating the expression of activation molecules on the surface of the immune cells; and (iv) evaluating the level of one or more immunoregulatory enzymes within the immune cells. A variety of cytokines, immunoregulatory enzymes, or activation molecules can be used, depending on the immune cells being evaluated. For example, if T-cells are being evaluated, the cytokines, immunoregulatory enzymes, or activation molecules known to be associated with T-cell activation should be evaluated. In some embodiments where the expression of activation molecules on the surface of the immune cells is evaluated, and the activation molecules are immune checkpoint inhibition receptors. Examples of activation molecules on the surface of immune cells are shown in Table 1.

The method of identifying autoimmune-affecting drugs also includes the step of determining that the candidate compound is an immune activating compound if the step of evaluating immune activation of the immune cells indicates that the immune cells were enhanced or potentiated by the candidate compound. Typically, evaluation of immune activation of the immune cells compares the activation of the immune cells in the absence of the candidate compound (as a control value) to activation of the immune cells in the presence of the candidate compound, and if greater enhancement or potentiation of the immune cell is seen in the presence of the candidate compound as compared with the control value, the candidate compound is characterized as an immune activating compound. In embodiments where the candidate compound is a non-immune affecting drug, the immune activating compound can also be characterized as an autoimmune-affecting drug, as described herein.

In addition, analogs of drugs that induce autoimmune phenomena may be selected for an increased capacity to enhance immune responsiveness and/or a decreased spectrum of off-target or adverse activities. For example a drug that is used as an anti-hypertensive agent with the side-effect of autoimmune phenomena is an autoimmune-affecting drug of the present invention. In the scheme described herein, this drug will be used with immune enhancement as the on-target effect, making its anti-hypertensive activity as an off-target effect. Analogs, isomers, or metabolites of such compounds could be selected to optimize the enhancement of the immune response (on-target effect) and minimize the anti-hypertensive activity (the off-target effect).

Administration and Formulation

The present invention also provides pharmaceutical compositions that include autoimmune-affecting drugs as an active ingredient, and a pharmaceutically acceptable liquid or solid carrier or carriers, in combination with the active ingredient. Any of the compounds described above as being suitable for stimulating immunity can be included in pharmaceutical compositions of the invention.

The autoimmune-affecting drugs can be administered as pharmaceutically acceptable salts. Pharmaceutically acceptable salt refers to the relatively non-toxic, inorganic and organic acid addition salts of the autoimmune-affecting drugs. These salts can be prepared in situ during the final isolation and purification of the autoimmune-affecting drugs, or by separately reacting a purified autoimmune-affecting drug with a suitable counter-ion, depending on the nature of the compound, and isolating the salt thus formed. Representative counter-ions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more autoimmune-affecting drugs together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The autoimmune-affecting drugs can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the autoimmune-affecting drug, or as a solution or suspension in an aqueous liquor or non-aqueous liquid such as a syrup, an elixir, an emulsion, or a draught. Such compositions and preparations typically contain at least about 0.1 wt-% of the active agent. The amount of autoimmune-affecting drug (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of enhancing the immune responsiveness of a subject having a deficient immune response, comprising administering to the subject a therapeutically effective amount of a drug known to induce one or more autoimmune syndromes, or an analog thereof, which is also known to induce one or more autoimmune syndromes.

2. The method of claim 1, wherein the drug is a drug selected from the group consisting of anti-arrhythmic drugs, anticoagulants, antihistamines, anti-seizure drugs, antihypertensive drugs, anti-inflammatory drugs, antibiotics, cholesterol-lowering drugs, hormonal drugs, laxatives, proton-pump inhibitors, psychiatric drugs, calcium channel blockers, vasodilators, anti-platelet drugs, and chelating agents.

3. The method of claim 1, wherein the drug is an immune checkpoint inhibitor blocker.

4. The method of claim 1, wherein the autoimmune syndrome is a lupus-like syndrome.

5. The method of claim 1, wherein the subject has a disease responsive to immune stimulation.

6. The method of claim 5, wherein the disease responsive to immune stimulation is selected from the group consisting of cancer, infection, immunodeficiency, immunosuppression, and Alzheimer's disease.

7. The method of claim 5, wherein the subject has been diagnosed with cancer.

8. The method of claim 5, wherein the subject has been diagnosed with a viral infection.

9. The method of claim 5, wherein the subject has been diagnosed with a bacterial infection.

10. The method of claim 6, wherein the subject has primary immunodeficiency or immunodeficiency acquired from infection.

11. The method of claim 6, wherein the subject has immunosuppression caused by aging, alcoholism, trauma, surgery, transplantation, splenectomy, diabetes, hepatic insufficiency, or protein-losing enteropathy.

12. The method of claim 6, further comprising administering to the subject a therapeutically effective amount of a pharmaceutical agent for treatment of the disease to the subject in combination with the drug known to induce one or more autoimmune syndromes, or an analog thereof, which is also known to induce one or more autoimmune syndromes.

13. The method of claim 1, wherein a plurality of drugs known to induce one or more autoimmune syndromes are administered to the subject.

14. The method of claim 1, further comprising taking one or more blood samples to assess the immune responsiveness of the subject after administering to the subject a therapeutically effective amount of drug known to induce one or more autoimmune syndromes, or an analog thereof, which is also known to induce one or more autoimmune syndromes.

* * * * *